United States Patent
Yu et al.

(10) Patent No.: US 10,248,756 B2
(45) Date of Patent: Apr. 2, 2019

(54) ANATOMICALLY SPECIFIC MOVIE DRIVEN MEDICAL IMAGE REVIEW

(71) Applicant: Siemens Healthcare GmbH, Erlangen (DE)

(72) Inventors: Daphne Yu, Yardley, PA (US); Shaohua Kevin Zhou, Plainsboro, NJ (US); Thomas Friese, Munich (DE); Klaus Engel, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/018,339

(22) Filed: Feb. 8, 2016

(65) Prior Publication Data

US 2016/0239632 A1 Aug. 18, 2016

Related U.S. Application Data

(60) Provisional application No. 62/117,715, filed on Feb. 18, 2015.

(51) Int. Cl.
*A61B 1/00* (2006.01)
*G06F 19/00* (2018.01)
*G16H 50/50* (2018.01)

(52) U.S. Cl.
CPC ............. *G06F 19/00* (2013.01); *G16H 50/50* (2018.01)

(58) Field of Classification Search
USPC .................. 386/223–224, 239–248
See application file for complete search history.

(56) References Cited

U.S. PATENT DOCUMENTS

| | | | | |
|---|---|---|---|---|
| 6,928,314 B1* | 8/2005 | Johnson | ............. | G06T 15/08 128/920 |
| 7,794,396 B2* | 9/2010 | Gattani | ............. | H04N 5/23296 348/65 |
| 8,682,576 B2* | 3/2014 | Kurtti | ............. | G01C 21/3476 701/426 |
| 9,129,390 B2* | 9/2015 | Dewaele | ............. | G06T 7/168 |
| 2005/0033162 A1* | 2/2005 | Garibaldi | ............. | A61B 1/00158 600/429 |
| 2006/0074275 A1* | 4/2006 | Davidson | ............. | A61B 1/04 600/160 |
| 2008/0012856 A1 | 1/2008 | Yu et al. | | |
| 2008/0071142 A1* | 3/2008 | Gattani | ............. | A61B 1/0005 600/117 |
| 2011/0050848 A1* | 3/2011 | Rohaly | ............. | G06T 15/10 348/43 |
| 2011/0274323 A1* | 11/2011 | Klingenbeck | ............. | A61B 5/0084 382/128 |
| 2015/0146946 A1* | 5/2015 | Elhawary | ............. | G06T 19/006 382/128 |

(Continued)

OTHER PUBLICATIONS

Liu, David, et al. "Search strategies for multiple landmark detection by submodular maximization." Computer Vision and Pattern Recognition (CVPR), 2010 IEEE Conference on. IEEE, 2010.

*Primary Examiner* — Hung Q Dang

(57) ABSTRACT

Generating anatomically specific movie driven medical image review is provided. Scan data is received representing an anatomy of a patient. A movie generation preset selection associated with the scan data is received. Anatomical landmarks within the scan data are detected. A movie of the patient is generated based on the scan data, the movie generation preset, and the anatomical landmarks.

22 Claims, 7 Drawing Sheets

(56) References Cited

U.S. PATENT DOCUMENTS

| | | | |
|---|---|---|---|
| 2016/0004412 A1* | 1/2016 | Meyer | G06F 3/0484 345/581 |
| 2016/0066768 A1* | 3/2016 | Popovic | A61B 1/00006 600/102 |
| 2016/0354158 A1* | 12/2016 | Razavi | A61B 34/20 |
| 2018/0368917 A1* | 12/2018 | Dekel | A61B 34/20 |

* cited by examiner

ANATOMICALLY SPECIFIC MOVIE DRIVEN MEDICAL IMAGE REVIEW

CROSS-REFERENCE TO RELATED APPLICATION

This application claims the benefit of the filing date under 35 U.S.C. § 119(e) of U.S. Provisional Application No. 62/117,715, filed Feb. 18, 2015, which is hereby incorporated by reference.

BACKGROUND

The present embodiments relate to generating anatomically specific movie driven medical image review. Images and data captured by medical imaging devices for medical image review may be collected, organized, manipulated, and output in data formats such as multi-dimensional renderings or static images. One example of multi-dimensional renderings is a 3D model rendered as a movie (e.g., a short video sequence lasting less than one minute) from digital medical image scan data. Movie sequences provide an opportunity to present medical image data focusing on specific areas of anatomic interest and enhance desired views providing detail and context that is not readily apparent in scan data and/or cannot be achieved through static images alone. Movie driven generation of anatomically specific output data may include both image processing techniques and movie generation and editing techniques to provide a visualization of scan results that are easily understood by patients while also providing detailed imagery aiding in review, examination, and diagnosis by medical professionals.

Conventionally, medical image review is conducted through editing workstations and operated by a technician or medical professional. The operator generates the desired anatomical views of the medical image scan by manually selecting the proper field of view and resolution on the region of interest of the patient by viewing and selecting anatomical regions of the medical image scan in graphical user interfaces of the editing workstation. In some conventional systems, the operator inputs individual instructions for rotation, zoom, pan, scrolling, clipping and masking via a graphical user interface, manually editing individual frames of the images, and manually providing individual instructions associated with sets of images. Other viewing parameters such as volume rendering, window level, surface color and opacity are interactively selected by the user as individual parameters or groups of parameters to highlight relevant structures and disease characteristics within the images. This examination practice is time intensive for the operator, requiring specialized training and experience based on medical imaging knowledge, for analysis. Alternatively, some conventional workstation systems provide a manual movie generation option to allow for trained technicians to pre-generate a movie sequence, which are then subsequently analyzed by medical experts.

BRIEF SUMMARY

By way of introduction, the preferred embodiments described below include methods, systems, instructions, and computer readable media for generating anatomically specific movie driven medical image review.

A method is provided for generating anatomically specific movie driven medical image review. Scan data is received representing an anatomy of a patient. A movie generation preset selection is received associated with the scan data. Anatomical landmarks are detected within the scan data. A movie is generated based on the scan data, the movie generation preset, and the anatomical landmarks.

Data representing instructions stored on a non-transitory computer readable storage medium are provided. The instructions may be executable by a programmed processor for generating anatomically specific movie driven medical image review. The instructions include receiving scan data representing an anatomy of a patient. The instructions also include receiving a movie generation preset associated with the scan data. At least one classifier is applied to the scan data based on at least one parameter of the movie generation preset associated with the scan data. The instructions further include identifying at least one first landmark based on the at least one classifier and generating a movie based on the scan data, the movie generation preset, and the identified landmarks.

A system for generating anatomically specific movie driven medical image review is provided. The system includes an imaging system configured to collect scan data representing anatomy of a patient. A processor is further included configured to detect anatomical landmarks represented by the scan data. The processor further generates a movie sequence rendered from the scan data, the rendering being based on the anatomical landmark and a preset group of parameters for the scan data.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, with emphasis instead being placed upon illustrating the principles of the invention. Moreover, in the figures, like reference numerals designate corresponding parts throughout the different views.

FIG. 3A is an illustration representing scan data in accordance with one embodiment for generating anatomically specific movie driven medical image review;

FIG. 3B is an illustration of FIG. 3A with anatomical landscape identification;

FIG. 3C is an illustration of FIG. 3B after key values have been selected to guide the movie data;

FIG. 3D is an illustration of movie image frames based on the representative scan data of FIGS. 3A-3C and based on key values to create a movie.

DETAILED DESCRIPTION AND PRESENTLY PREFERRED EMBODIMENTS

Figure 1:
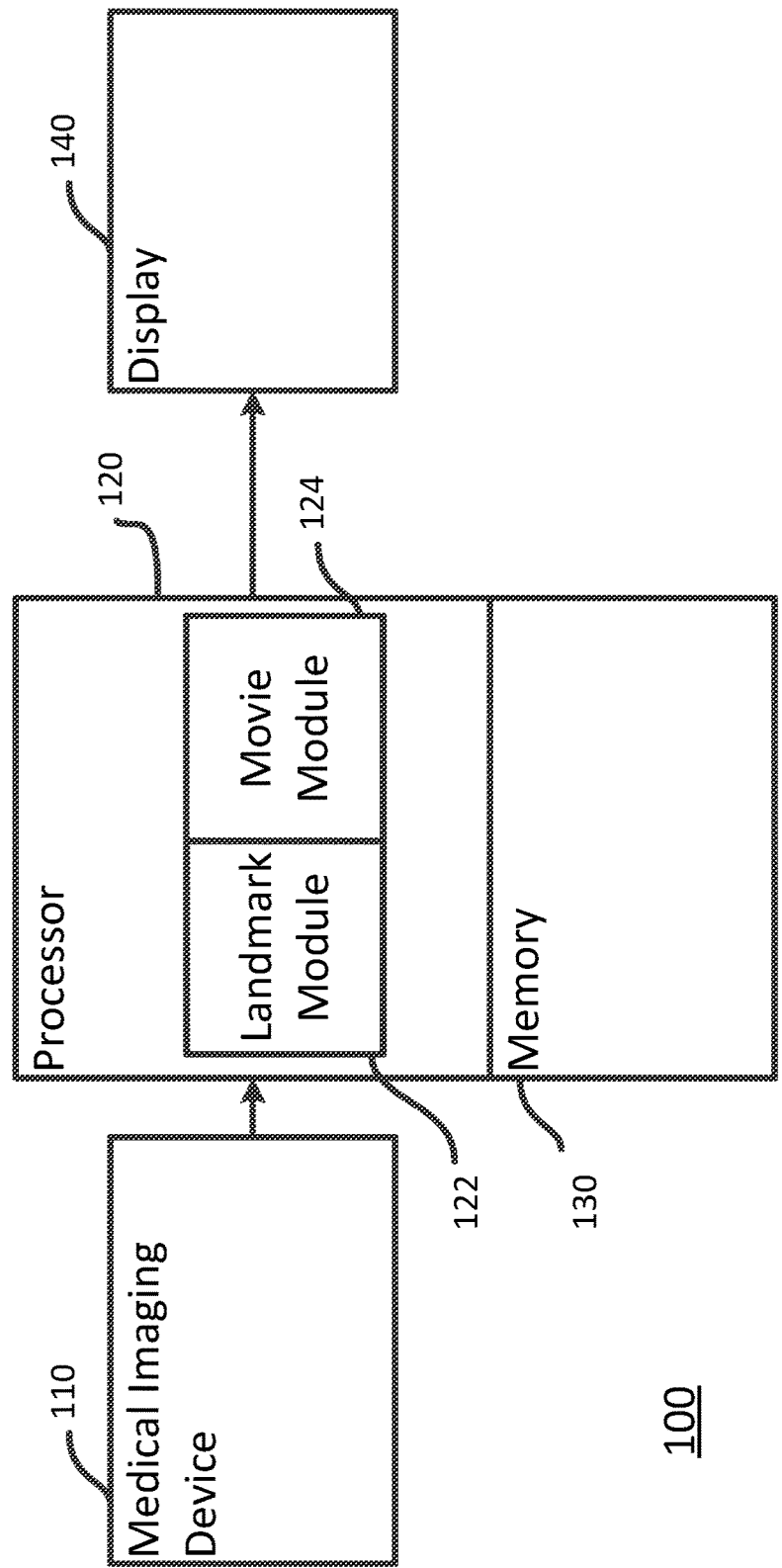
FIG. 1 is a block diagram of one embodiment of a system for generating anatomically specific movie driven medical image review.

Physical limitations of specialized medical imaging generation and medical imaging review workstations have been addressed in the conventional art through the use of virtual machine application deployment or the use of simplified applications accessible via the Internet. These image generation and review workstations require a high level of operator skill and experience to generate and review high quality medical imagery and movie sequences. Construction and review of movie sequences is a detailed and labor intensive process requiring the operator to select multiple individual components to visualize each individual patient scan. Simplification of movie sequence generation, increased efficiency of medical personnel, and reduction in training time of medical personnel are desirable to meet increasing demand for medical imaging movie sequences as a robust medical diagnostic tool.

A goal of the disclosed embodiments is to automate and/or simplify manual interaction of the operator when generating anatomically specific, movie sequence imagery for medical image review. A goal of the disclosed embodiments is to provide a system and method using known information associated with scan data, the medical workflow protocol, and medical diagnostic needs to enhance, automate, and simplify image processing techniques identifying anatomical landmarks in scan data. A goal of the disclosed embodiments is to use such known information to also enhance, automate, and simplify the selection of generation of multi-dimensional models from the identified landmarks. Yet another goal of the disclosed embodiments is to further enhance, automate, and simplify the selection of parameters to generate a movie sequence featuring the multi-dimensional model. Still yet another object of the provided embodiments is the efficient optimization of perspective, resolution, field of view, zoom, sequence, and masking parameters used in the creation of movie sequences. Yet another goal is to provide an efficient approach for a wide variety and combination of imaging device modalities, imaging workflows, and medical protocols.

Embodiments for generating anatomically specific movie driven medical image review are provided. The disclosed embodiments facilitate automation and simplification of landmark identification and movie sequence generation. Advantages are achieved, in part, by constructing and selecting parameters for landmark identification and movie generation from known information sources including metadata associated with scan data sets, workflow information, and protocol information associated with the patient's case. Movie generation presets are sets of parameters associated with one or more scan data sets captured by a medical imaging device. The parameters provide details required to automatically select settings for landmark identification and movie generation. Through landmark identification and movie generation, the correct anatomical region is identified, and the camera settings for the movie sequence is optimized. Scan data is further filtered, smoothed, refined, and manipulated based on the movie generation presets for rendering and movie encoding. Review of the generated movie may include additional interaction with the generated movie, such as adding notation, selection of areas within frames, or marking segments of the movie.

Generated movie data may be stored as files or streams and/or provided for display upon completion of rendering. Movie data files may be transmitted via network for display and for medical review and analysis by a medical professional. Upon medical review, analysis, or diagnosis, points of interest may be selected by the medical professional and stored with the movie data. The movie data file may be further manipulated and updated for further interactive examination for medical professionals. Review based additions, selections, or revisions may be re-entered in the disclosed system in order to re-render the movie sequence based on review. Review information may additionally or alternatively be appended to the movie sequence. In some embodiments, movie data may also be stored in data formats compatible with non-application specific media players. Copies of the movie data and/or movie data with identified points of interest to a patient may be compatible with conventional media players, including personal computers, mobile devices, tablet computers, televisions, video game consoles, dvd players, Blu-ray players and the like.

The need for an operator to manipulate and carefully choose the appropriate field-of-view and case specific parameters in individual image frames is greatly reduced. In this movie driven workflow, a user (e.g., one or more operator of components of the disclosed system) selects from a set of movie generation presets. One or more movie generation presets may be preferred for specific anatomical regions of interest, types of medical conditions, and/or specific imaging modality. Additionally, movie generation presets may specify sets of parameters that control movie generation. Such parameters could include the preferred transfer function, window level, color, lighting and materials, preferred point of view sequence and scaling relative to the anatomy, clipping away certain structures etc. The medical image data is rendered using 2D, 3D, 4D image rendering techniques based on descriptors and/or parameters in the selected movie generation presets. Descriptors of a movie generation preset include data specifying the anatomical features of interest and the parameters suitable for viewing the specific anatomical features. Movie sequence generation is partially or fully automated based on the scan data content and the selected movie generation preset. The generated movie presents a sequence of images to optimally view the anatomy of interest. In one non-limiting example, one movie generation preset provides the necessary parameters to direct the system to create a movie sequence from a contrast enhanced CT scan. The generated movie sequence includes a 360-degree view of a 3D heart based on the CT scan data. Rendering parameters optimized for the review of coronaries within contrast enhanced CT scans. Another non-limiting example of a selected movie generation preset provides parameters to produce a movie sequence of an obliquely reformatted planar view showing a 2D cine view aligned with the long axis of the left ventricle of the heart. Another non-limiting example provides a panoramic view along the spine progressing from top to bottom. Multi-perspective or side-by-side comparison views may also be specified in descriptors contained in the movie generation preset. Accordingly, once a movie generation preset is selected by the operator of the system and the scan data has been received by the system, anatomical landmarks designated by the selected presets are automatically selected. Further notation from the operator of the system identifying regions of interest or specific anatomy through a graphical user interface is reduced or eliminated.

The generated movie may be encoded with corresponding metadata for the generation parameters. In this case, the movie sequence of the system may be additionally compatible with other customized applications, programs, or workstations. Users may then review the movie sequence that has been automatically generated and further select specific playback time and screen position(s), marking one or more points, frames, or regions of interest within the movie. The annotated movie sequence may be further encoded such that the annotated movie sequence with corresponding metadata may be stored for later use or transmitted to another user for further examination of the selected points or region. The generated movie may include additional functionality so that the user may open a secondary interactive viewer and review or examine selected areas in the original scan data for detail in the traditional workflow.

A preferred embodiment may include receiving medical image data as a stack of 2D images for generation into a 3D model. Another preferred use case includes receiving multiple stacks of 2D images captured over a period of time for generation into a 4D model (i.e., 3D plus time). Data scan input may include multiple volumes to model changes in patient anatomy over time or monitor the progress of a treatment regimen. These embodiments identified as preferred embodiments are non-limiting examples.

In these embodiments, movie sequences are then generated from the 3D and 4D models, respectively, for medical image review. A movie sequence may provide a sequence of varying views of the modeled 3D or 4D volume representative of patient anatomy. Varying views of the movie sequence in accordance with preferred embodiments may begin with a 360° rotation around the entire 3D or 4D volume. The movie sequence may include zooming into a particular region, area of interest, or target of the modeled volume. The movie sequence may additionally provide a 360° rotation of the identified region, area, or target at a finer degree of resolution. The movie sequence may appear to mimic a video camera travelling around the modeled volume.

System Architecture

One exemplary system 100 for generating anatomically specific movie driven medical image review is illustrated in FIG. 1. System 100 includes a medical imaging device 110, processor 120, memory 130 and display 140. Processor 120 includes landmark module 122 and movie module 124. Additional, different, or fewer components may be provided. For example, a network or network connection is provided in some embodiments enabling networking with a medical imaging network or data archival system. As another example, the system 100 may be considered to include only processor 120 and memory 130. That is, processor 120 may receive medical imaging device data input from one or more devices outside of system 100. Processor 120 may generate movie sequences that are stored in memory 130. Movie sequences may be transmitted for display one or more devices outside of system 100. Movie data generated by processor 120 and/or stored on memory 130 may be transmitted to other memory, database, or other storage devices of system 100 not depicted in the figure. The processor 120 may transmit movie sequence data to a device or display outside of system 100 without storing movie sequence data in memory 130.

Some or all components in the system 100 may be physically connected, electrically connected, communicatively connected via a wired or wireless network, or a combination thereof. Some or all components of the system 100 may be integrated in a system housing multiple components in one physical frame. Additionally, or alternatively, one or more components of the system 100 may be remotely located. System 100 may include multiple sets of components functioning as work stations (e.g., diagnostic imaging workstations, clinical review workstations, and dedicated 3D viewing workstations) in addition to multiple sets of components functioning as medical imaging devices.

The processor 120 and/or display 140 may be part of a medical imaging system or device 110, such as an ultrasound, x-ray, computed tomography (CT), magnetic resonance imaging (MRI), or positron emission tomography (PET), single photon emission tomography (SPECT), ultrasound, x-ray, or other medical imaging system. Alternatively, the processor 120 and display 140 are part of an archival and/or image processing system, such as associated with a medical records database workstation or server. In other embodiments, the processor 120 and display 140 are a personal computer, such as desktop or laptop, a workstation, a server, a network, or combinations thereof. The processor 120, display 140, and memory 130 may perform some or all of portions of method embodiments.

Memory 130 is a graphics processing memory, a video random access memory, a random access memory, system memory, random access memory, cache memory, hard drive, optical media, magnetic media, flash drive, buffer, database, combinations thereof, or other now known or later developed memory device for storing data or video information. Memory 130 is part of an imaging system, part of a computer associated with the processor 120, part of a database, part of another system, a picture archival memory, or a standalone device. Memory 130 may include multiple components, including remote databases. Memory 130 may be partitioned and include multiple databases. One or more memory 130s may be integrated with processor 120, remotely accessible by processor 120, integrated with other components of the system. One or more components of system may include memory 130. For example, medical imaging device 110 may include a memory 130 storing data remains on the memory of device 110 while in use with processor 120.

Memory 130 stores scan data, image data, or other sensor based data representing a region of a patient. The representative region may be obtained in multiple scans from one or more medical imaging devices 110 to create a single 2D, 3D, or 4D model of the representative region of the scan. The region is a two or three-dimensional region. The region may be defined by geometric or anatomic boundaries. A region may be defined as any part of a patient, such as a region within the chest, abdomen, leg, head, arm, or combinations thereof. The region may constitute the entire patient. The region represented in scan data may be larger (or smaller) than the resulting, desired model.

Scan data is captured by scanning the region by any medical imaging device 110 or a combination of medical imaging modalities. The medical imaging device 110 captures the scan data. As such, the medical imaging device 110 is a CT, MRI, PET, SPECT, ultrasound, x-ray, or other medical scanner. A scan data set may include data from one or more sources or scans from medical image data including ultrasound produced image files, x-ray, CT, MRI, or PET data. Examples of patient regions and patient volumes include, but are not limited to: an organ scan (e.g., the heart), one or more bones (e.g., the spine), or a region (e.g., limb, torso, patient area affected by trauma, geometrically defined area of a patient, area of the patient defined by a boundary, or any other area of interest).

Scan data may be representative of the patient prior to, during treatment, and/or following treatment. For example, medical image scans may be taken to aid in diagnosis, planning of treatment, or post treatment assessment. Data may be collected at multiple stages of patient care and/or from multiple medical imaging modalities.

Scan data is data that can be used to generate an image, pixels values to be displayed, pixel values that were displayed, or other frames of data representing the region of the patient at a given time, duration of time, or multiple different times. The image data may be frames of Digital Imaging and Communications in Medicine (DICOM) format data or frames of data generated along any portion of a data processing path of an imaging system, such as the medical imaging device 110. A sequence of frames of data may be acquired, such as acquiring images over a period of time, over one or more periodic cycles of the body (such as breathing cycle or heart cycle) and may be captured at any frame rate (e.g., 10-30 frames per second).

Alternatively, or additionally memory 130 stores one or more databases of landmark identification information (e.g., databases containing multiple trained object classifiers for use with landmark module 122), databases including multiple movie generation presets for selection by a user or for selection by processor 120, and/or databases of movie rendering information (e.g., image processing filters associated with movie module 124).

The memory 130 or other memory is alternatively or additionally a computer readable storage medium storing data representing instructions executable by the programmed processor 120 for generating anatomically specific movie driven medical image review. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 120 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for generating movie sequences of anatomy from medical imaging device data. The processor 120 is a single device or multiple devices operating in serial, parallel, or in tandem. The processor 120 may be a main processor of a computer, such as a laptop or desktop computer, or may be a processor for handling some tasks in a larger system, such as in an imaging system. The processor 120 is configured by instructions, design, hardware, and/or software to be able to perform the acts discussed herein.

Processor 120 includes landmark module 122 and movie module 124. Additional, different, or fewer modules may be used. Modules 122 and 124 may be software modules, hardware modules, or a combination of software and hardware modules. Landmark module 122 performs image processing operations to detect one or more anatomical landmarks within the scan data received by processor 120 from medical imaging device 110. Landmark module 122 may receive scan data directly from medical imaging device 110, from memory 130, or from multiple medical imaging devices, memory, or combinations thereof. Landmark module 122 identifies multiple landmarks within the scan data by employing a multiple landmark detection algorithm. A landmark may be a point, region, or bounded area.

In one or more embodiments, the landmark module 122 also receives information associated with the received scan data in the form of metadata. Metadata includes information generated, associated, and/or transmitted with the scan data by the medical imaging device 110. Metadata may further be received from memory 130 and may be movie generation presets. Metadata may also be included or associated with movie generation presets stored on memory 130. Metadata is used to optimize the order of application of trained object classifiers used to detect landmarks of interest. In one embodiment, metadata is generated, received, and/or associated with the scan data by processor 120 and may include data also associated with movie generation presets to optimize landmark identification based. Optimization may be associated with selection of one or more classifiers, elimination of regions of scan data for further processing by landmark module 122 or movie module 124. Hierarchical organization of landmark classifiers may be based on landmarks associated with a hierarchy of anatomical regions and/or the spatial relationship between one or more anatomical regions. Hierarchical organization of landmark classifiers may include order of application based on positive landmark identification during analysis of the scan data. In other embodiments, landmark module 122 optimizes application of landmark classifiers based on data from at least one movie generation preset associated with the scan data. In still yet other embodiments, multiple landmark identification optimizations may be employed serially or in parallel.

Landmark module 122 generates anatomical landmark data associated with the scan data including a set of anatomical landmarks, one or more defined region of the scan data, image processing data (e.g., segmentation label regions), extracted surfaces, graphical markers for points of interest, and/or positional registration identification data points for registration related scan data sets (such as scan data with a temporal dimension). Data generated by landmark module 122 may be associated with the time step of each landmark defined in the descriptor. Landmark module 122 may further employ additional filtering, frame generation, data interpolation or a combination of additional techniques. These additional processes of landmark module 122 smooth, refine, remove or estimate scan data to provide a higher quality model and result in higher movie quality.

Movie module 124 renders a multi-dimensional model representing the area of interest from scan data, detected anatomical landmarks, and a movie generation preset. Movie module 124 also receives, identifies, generates, interprets, and/or applies parameters based on scan data, detected anatomical landmarks, and the movie generation preset to create the movie sequences of the multi-dimensional model for output from processor 120. Movie module 124 may establish and visualize the camera focal point and frustum based on the identified landmarks, metadata, and movie generation presets for the scan data. The movie module 124 further performs image processing and generation of movie frames for playback output by processor 120, storage in memory 130, and/or transmission for display 140. In some embodiments, the output data of the processor 120 provides output in a standard movie format that may be played using one or more media players or may be output in a standard movie format for transmission to intermediate devices for storage and/or use with media player devices and displays.

In other embodiments, the output data of the processor 120 provides output data that may include additional data (or may be formatted in alternative data formats) providing functionality with specialized movie players allowing for selection of points of interest or other interaction, manipulation, or editing of the movie data output from processor 120.

The display 140 is a monitor, LCD, projector, plasma display, CRT, printer, mobile device display, television, or other now known or later developed devise for outputting visual information. The display 140 receives images, video, graphics, or other information from the processor 120, memory 130, and/or medical imaging device 110. One or more images representing a portion of or all of the patient region of the scan may be viewed on display 140. Movie sequences generated by movie module 124 of processor 120 may be displayed on display 140.

Figure 4:
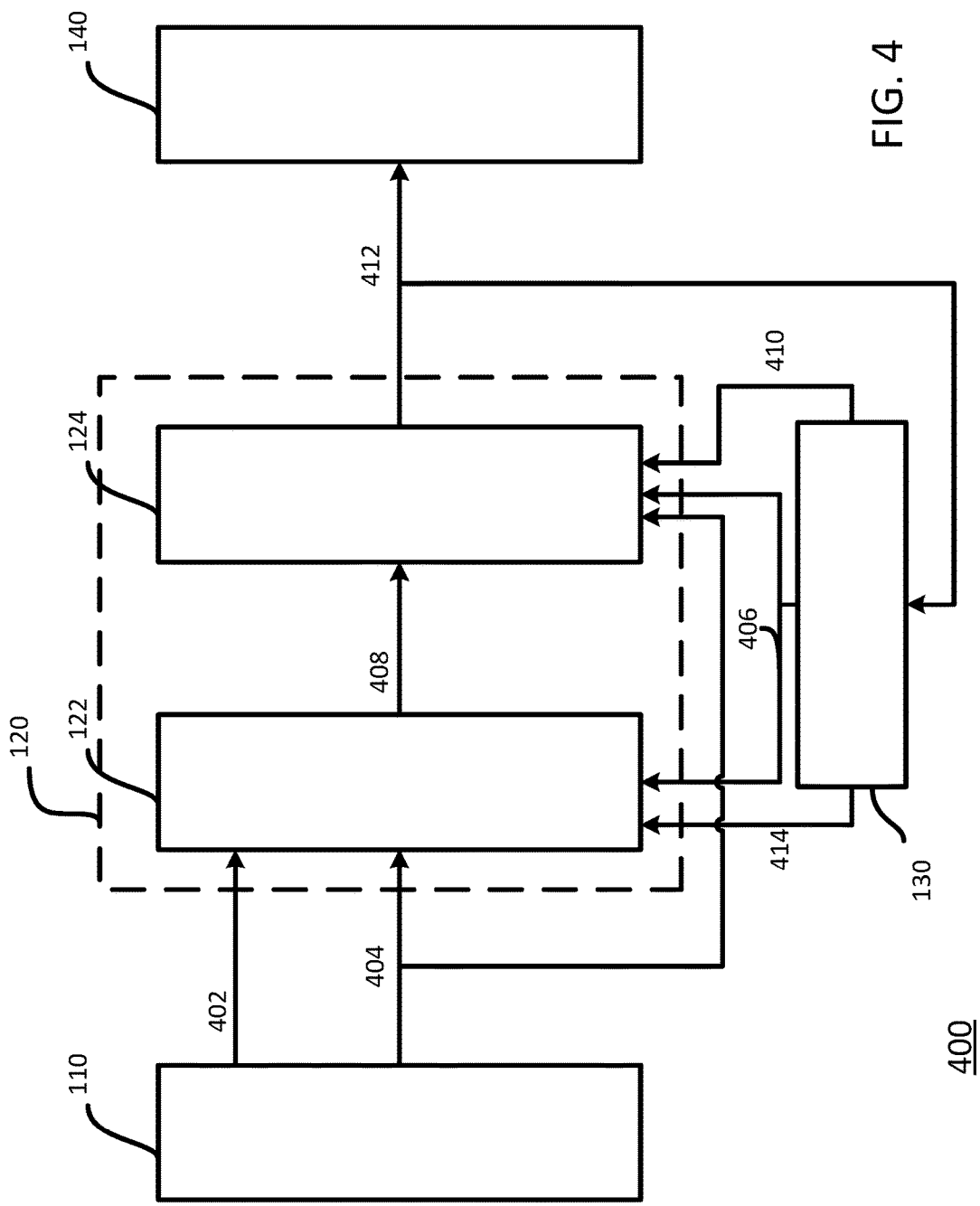
FIG. 4 is a data flow diagram of one embodiment of the method of FIG. 2 in accordance with the system of FIG. 1.

FIG. 4 is a data flow depicting one embodiment of input and output of the system of FIG. 1. FIG. 4 depicts the system 100 of FIG. 1: medical imaging device 110, processor 120 (including landmark module 122 and movie module 124), memory 130, and display 140.

Medical imaging device 110 outputs scan data 402 and metadata 404. Metadata 404 may also be input to movie module 124 alternatively. Scan data and metadata may be input into processor 120 or stored in a memory 130 and input into modules 122 and 124 from intermediate sources. Memory 130 may provide data input 406 into landmark module 122 and/or movie module 124. Data input 406 may include movie generation presets. Memory 130 may additionally store classifier data 414 for input into the landmark module 122. Landmark module 122 of processor 120 uses one or more of input data including scan data 402, metadata 406, classifier data 414, and movie preset data 406 in order to perform landmark identification. Output from landmark module 122 includes identified landmark data 408. Output from landmark module 122 may additionally include metadata, scan data, and/or movie generation preset data for input into the movie module 124. Movie module 124 may receive scan data and metadata 404 directly from the medical imaging device or from memory 130. Output 408 may also be stored in memory 130 and accessed by movie module 124 via memory 130. Point identification markers analysis or other data 410 acquired during movie playback and analysis for regeneration of the movie may be transmitted from memory 130 and may be used to re-render, update, append, or otherwise be associated with data generated with movie module 124. Output of movie module 124 includes movie data 412. Movie data may be provided for display on display 140. Analysis of the displayed movie may be entered and stored in memory 130 and then provided to movie module 124 via data 410. Output movie data is further representative of movies that have been re-rendered or altered following movie playback and medical analysis.

Components represented in FIG. 4 may be formed of multiple components. For example, memory 130 is representative of all storage associated with system 100 and may contain multiple discrete components. For example, components comprising memory 130 may be integrated with processor 120, may be integrated with medical device 110, may be put a part of a workstation containing display 140, and may be remote storage. One or more memories 130 may each be partitioned such that multiple databases are used as memory 130. For example, a database including classifier sets may be stored in one database in a memory 130 and movie generation preset data may be stored in another database of the memory 130. Further, memory 130 is representative of data storage systems that may store instructions for execution by processor 120 and/or its modules.

System Workflow and Method

Figure 2:
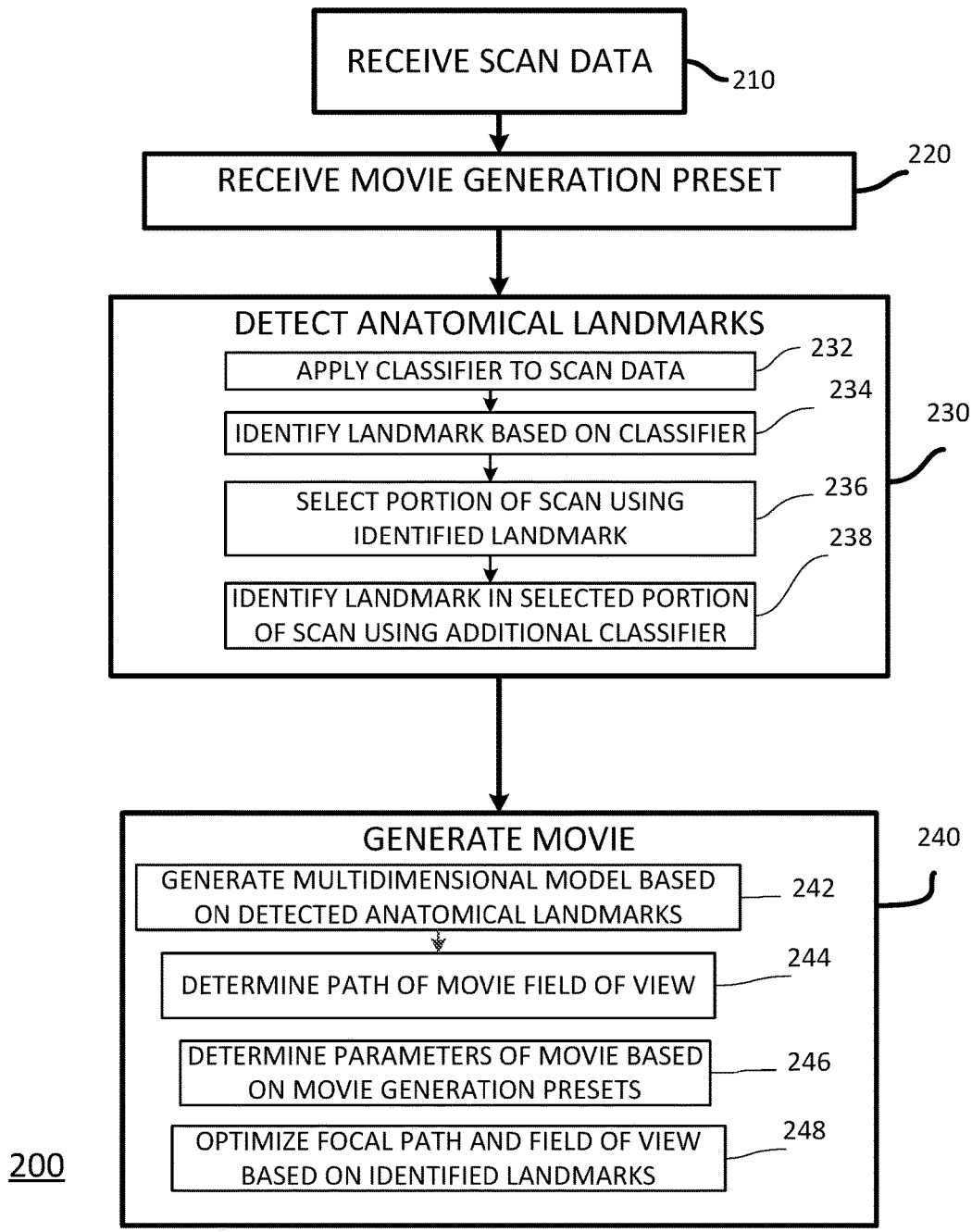
FIG. 2 is a flow chart depicting one embodiment of a method for generating anatomically specific movie driven medical image review.

FIG. 2 is a flow chart illustrating a method 200 for generating anatomically specific movie driven medical image review implemented by system 100 or another system. The acts of the method may be implemented entirely or in part by processor 120 in interaction with the medical imaging device 110, the memory 130, the display 140, and/or other devices (e.g., network or network interface). The method 200 provide diagnostically useful information. Scan data representing a patient is processed to generate a movie sequence that may provide diagnostically useful information not provided or provided as well by mere imaging of the medical imaging device 110.

Additional, different or fewer acts may be provided. For example, none, some, or all acts shown within acts 230 and 240 may be performed. As another example, steps 232, 234, 236, and 238 may be repeated using multiple sets of classifiers in a hierarchy until all landmarks have been identified. The acts are performed in the order shown or another order or at the same time. For example, multiple acts of landmark identification 230 may be carried out at the same time.

In act 210, scan data is received. Scan data is received by processor 120 from a medical imaging device such as medical imaging device 110. In act 220, movie generation presets are received. Movie generation presets are received by the processor 120 from medical imaging device 110 and/or may be stored in memory 130 as a database of predetermined sets of movie generation presets. Any combination of presets may be used, such as a list of landmarks and associated classifiers to detect landmarks associated with a particular scan or type of scan. The presets are based on user selection, so are received from a user input. Alternatively, the presets are based on a default or scan settings of the medical imaging device 110, such as presets being in metadata from the device 110 based on the type of scan performed.

Anatomical landmarks are then detected in act 230. Specific anatomical landmarks detected in act 230 are anatomical features with distinct image appearances that may be reliably detected (e.g., trachea bifurcation). The landmarks are detected by application of a classifier, segmentation, image processing, algorithm, or other detector of anatomy from scan data. Multiple anatomical landmarks are detected within the scan data received from a medical imaging device 110 by the landmark module 122 of processor 120. The same or different landmarks are detected, such as detecting different landmarks associated with the heart. In one embodiment, anatomical landmark detection within the scan data includes applying at least one first classifier to the scan data in act 232 and identifying at least one first landmark based on the at least one first classifier in act 234. For time based scan data, landmarks may be detected for a representative scan, tracking any changes of landmarks in scans at other time stamps. Landmark identification may be performed independently for the scan data at each time stamp. The detection is applied independently or dependently for each time stamp. Alternatively, the detected landmark for one time is tracked using a tracking or different process in scan data of other times.

In another embodiment, portions of the scan data are selected based on the identified landmark by landmark module 122 of processor 120. The landmarks, in combination with the presets, indicate a region of interest for the movie. For example, different parts of the left ventricle are detected. Based on a tolerance or scale setting of the presets, a region covering these detected landmarks is designated as the region of interest for the movie. For example, the entire left ventricle is selected. The anatomical landmarks may also be used to mask or clip away unwanted structures within the field of view within the sequence if described in the preset.

In act 240, a movie sequence is generated. Movie module of processor 120 generates and/or renders a movie based on scan data from a medical imaging device 110, one or more parameters of the received movie generation preset, and the detected anatomical landmarks. Camera settings, field of view and other characteristics of the movie sequence are determined based on the received movie generation preset. Position of the camera is determined based on key values, with key values determined based on the identified anatomical landmarks. The movie is rendered or imaged from the scan data. Parameters of the received movie generation preset indicate the region of interest. The landmarks are used to identify region of interest within the scan data. Locations outside the region may be segmented away (not included) or reduced in influence (e.g., made more transparent). The movie generation presets indicate the rendering settings to use, such as different transfer functions and/or window levels for different anatomy being imaged. In some cases, the preset may describe a general appearance that needs to be adapted to the specific data with varying contrast through optimizing the final parameters to preserve the described appearance. For example, the preset may describe a transfer function and a representative image, but the final parameterization of the transfer function to the specific data can be optimized based on some metrics to bring the results closer to the representative appearance. Various metrics can be used, mathematical based metrics such as simple mean square errors, or visual perceptual based metrics.

Generation of a movie in accordance with act 240 may further include generating a multidimensional model based on the detected anatomical landmarks in an act 242. In act 244, a path of the movie sequence field of view of the multidimensional model is determined based on the preset group of parameters and the anatomical landmarks. Parameters of the movie are determined based on movie generation presets in an act 246. Act 246 may be performed as a component of acts 242, 244, or any number of acts performed associated with generation of the movie in act 240. Generation of a movie in accordance with act 240 may further include optimizing a focal path and field of view of the movie based on the identified landmarks in an act 248. As part of act 248, optimization of the focal path and field of view of the movie may include determining obstructions within the path of the movie sequence field of view, removing obstructions within the path of the movie sequence field of view; and generating replacement imagery based on the removed obstructions, the scan data, and/or images of the movie sequence.

The acts of method 200 and other methods in accordance with the disclosed embodiments may be performed as detailed below.

Detection of General Dataset Type of Scan Data

Scan data may be inherently limited by constraints such as size of the patient, trauma, fractures, foreign objects, field-of-view, limitations in resolution based on focus, or device modality. Scan data quality may further be reduced because of patient movement and/or errors in operator control. That is, medical imaging device 110 may obtain scan data failing to render certain portions of the patient region due to the position of the patient relative to the medical imaging device, obstructions, and limitations of the resolution present in the initial scan data set.

Scan data, which may be generated by various modalities of medical imaging devices 110 may be received in a variety of dataset types. Accordingly, a general dataset type is detected by the processor 120. Scan data include meta data associated with the dataset type such as modality, intensity histogram or bit range, dimensionality (e.g., 2D, 3D, or 4D), scanner protocol, and the like. Alternatively, or additionally, the processor 120 may generate histograms directly from scan data image intensities or may analyze the provided scan data including any meta data to generate dataset type information. System 100 may automatically determine the purpose of the scan based on information available in metadata associated with the scan. System 100 and processor 120 may identify dimensionality of the received scan limiting available view options based on the original data set. If the purpose of the scan is determined based on metadata or other information, method 200 may automatically determine or reduce available preset options. Automatic determinations may be triggered based off of metadata included in the data scan, information received from a medical imaging device 110, and/or information entered by an operator interacting with a graphical user interface of processor 120. The user may be provided with the automatically determined information and presented with an option to override automatic determination or make further selections prior to, during, and/or after the completion of movie sequence generation.

Dataset type information may include information associated with the anatomy contained within the scan (e.g., head, abdomen, heart, spine). This information may be appended to scan data automatically by medical imaging device 110, input by an operator of medical imaging device 110, or may be detected from the scan data received by the processor 120. Processor 120 may include additional software modules for anatomical region identification (e.g., CT Vascular).

Selection of Applicable Movie Generation Presets for Scan Data

Movie generation presets include multiple classes of data. Data classes include movie scene descriptors consisting of a set of data, required data criteria that the descriptor is applicable to, and descriptors for movie scene parameters. Movie generation presets facilitate partial or complete automation for movie generation, furthering a goal of the disclosed embodiments of automating and simplifying the necessary manual intervention of a user or operator. Movie generation presets further another goal of the invention of reducing the necessary knowledge, skill, training, of user or operators of the system while required to obtain optimal movie output tailored to the medical examination and diagnosis needs of individual patient scans.

Examples of data criteria include, but are not limited to: applicable modalities, scan protocols, applicable data dimensionality (e.g., 2D, 3D, 4D, single or multiple datasets, time series), type of body part applicable (e.g., head, torso, all types).

Movie generation preset descriptors for movie scene parameters include, but are not limited to: anatomical landmarks (e.g., points and/or planes to define a path relative to the anatomy or the patient), orientation vectors of the camera described as relative coordinates to the landmarks, camera field of view (physical size), projection, focus, aperture, and exposure relative to each anatomical landmark within the movie sequence, objects that should be visible or hidden via masking (e.g., anatomical parts, examination equipment, or implants), visible region of data (e.g., clip away outer boundary of dataset, or clip along center), intensity classification of the image data (e.g., color lookup tables, window level), material properties of specific object classification (e.g., color of anatomical objects or tissues), light model, lighting direction, light maps, exposure settings, white balance, type of view (e.g., planar view, 3D volume rendering, 3D surface of extracted structures, type of rendering (e.g., direct ray casting, ray tracing, image based), and/or selected time steps (if the data is in a time series containing a temporal component) relative to events such as body process cycles (e.g., heart cycle, breath cycle). Different presets are provided for different types of scanning and/or scans of different parts of the patient.

Preset selections of movie generation presets may be identified by the organ of interest, particular view perspectives, diagnostic information and the like. For example, one set of movie generation presets may provide movie generation of a 360° view of a 3D model. Other movie generation presets associated with view degree include slice view, one point of time and the like. Upon operator selection of the movie generation preset, the graphical user interface of processor 120 may request specific input from the operator such as a starting location or identification of a view degree 360°. Additional information associated with a 360° walk around may include resolution of the degrees or location and thickness of a selected slice view. Orientation relative to the patient may additionally be relevant. Default selections of these types of parameters may be provided. The graphical user interface may prompt the user to select a set of default values for these parameters where the user may select one of multiple provided options of popular values. The generation of the 3D model may include a slice model at one point in time. Additional parameters include the number of degrees selected for review, resolution, and perspective. Perspective of the anatomy may be based on metadata or known other presets. Another example includes a panoramic view of an organ region or area (e.g., panoramic view along the spine). Orientation of the patient with respect to the scan data may be provided in metadata or determined by processor 120. Optimal rendering targets may be determined (e.g., a review of coronaries within a contrast-enhanced CT scan). Another example includes obliquely reformatting a planar view showing a 2D cine view aligned with the longitudinal axis of the left ventricle of the heart.

A user may be presented with predetermined sets movie presets via a graphical user interface. Presets may be selected by an operator of the system 100, and/or may be automatically generated by medical imaging device 110 as metadata during or following image acquisition. Movie generation presets for a single set of scan data may be automatically determined by processor 120. Movie generation presets may be generated, received, or selected from any combination of the above disclosed sources. The user may be presented with predetermined sets of movie presets that may be grouped based on anatomical region, desired medical image review, and the like. A user may further make or customize the predetermined sets of movie presets for a set of scan data via a graphical user interface of the processor 120. Processor 120 may narrow the selection of available predetermined sets of movie presets based on detection of scan data dataset type information from metadata, or determined by processor 120.

Automatic selection may be configured by set of rules executed by the processor 120 based on workflow or medical protocol. Predetermined sets of filters may be pre-selected and optimized for particular medical protocols.

Parameters for the movie are determined in order to optimize the type of medical review desired. For example, patient scans may be taken for visualization and evaluation of a tumor. Presets describing the parameters are then grouped so that the parameters are best suited for the medical review intended. Rendering parameters, identification of organs of interest, and preferred point of view may be derived from the movie preset descriptors.

Anatomical Landmark Detection

Initial landmark detection of landmark module 122 provides a coarse landmark data set identifying anatomy and position. Individual characteristics of the patient's anatomy, injury, abnormalities, and/or scan data quality may affect the number of landmarks that are detected.

Anatomical landmark detection is image processing performed by landmark module 122 using object classifiers constructed via machine learning methods, but other detection may be used. Classifiers are trained using training scan data with identified individual anatomical landmarks as positive examples and non-landmark locations as negative examples. Through training, landmark locations may be manually positioned and cropped with a window around the positive locations. A database of trained classifiers may be provided to system 100.

The group or set of trained classifiers may be determined with a predetermined workflow. In the broadest sense, an iterative approach may be applied in which each classifier is independently applied the scan data to determine each landmark. In this approach, the detection of a landmark with one classifier does not inform or affect the application of other classifiers in the set.

In another approach, classifier sets have hierarchical relationships such that one or more first classifiers are applied to the scan data to form a base layer. Once landmarks in the base layer are identified, the base layer landmarks form constraints for detecting landmarks in higher layers. That is, upon determination of base layer landmarks, a smaller region is determined for application of subsequent sets of classifiers. Subsequent sets of classifiers may be determined based on parameters of the region defined in base layers. Multiple sets of classifiers may be used to form higher layers of landmark detection. Spatial constraints between landmarks may be leveraged for detection efficiency.

For example, in this approach, a first set of classifiers is applied to the entire scan data set (e.g., scan data of a torso). Upon detection of the first landmark (e.g., identifying location of the heart), known anatomical relational information, such as the proximate location of other organs (e.g., left and right lung) to the heart may be used to constrain additional layers in the classifier hierarchy. The scan data set may then be segmented for additional landmark layers such that sets of classifiers identifying left lung features are applied to the segmented region in which the left lung is expected to be found based on the location of the heart landmark. Proximate relationships may be used to determine the constraints and locations of higher layer areas such that orientation data of the scan are not necessary for application of sets of classifiers. In this manner, relational information of one or more landmark layers is used to select and determine other classifiers for increasingly segmented portions of the scan until all relevant landmarks have been identified or until all applicable classifiers or a determined set of classifiers have been applied to the scan data. In this approach, subsequent sets of classifiers are not selected based on workflow context, but instead based on base layer identification.

The scan data set may be processed using multiple sets of trained classifiers. The set of trained classifiers may be determined based on scan data metadata and/or movie generation presets. For example, scan data identifying an anatomical region of the scan may be used by processor 120 to select landmark classifiers for appropriate anatomical landmarks of the scan region. In one embodiment, the determined set of classifiers is individually applied to the scan data. Identified anatomical landmarks may be used to form a base layer facilitating hierarchical detection using the set of classifiers. Base layer landmarks are detected and form constraints for detecting landmarks in higher layers. When detecting the set of landmarks within one layer, the spatial constraints between these landmarks may be leveraged for detection efficiency. In construction of the 3D model based on identified landmarks, regions areas, objects may be identified for removal.

Output of landmark module 122 may include a data set including anatomical landmarks, image masks, graphical markers, or other information identified or associated with landmark identification via module 122. A target region may further be specified by landmark module 122. Anatomical landmarks associated with the target region may be further identified.

In another preferred approach, workflow context is known based on meta data of the scan and/or movie generation presets. That is, the region of the body represented in the scan, and ultimate desired anatomical region of the generated movie is known. Context information is used to reduce the range of application of classifiers, or reduce constraints to provide accurate but computationally efficient application of classifiers for landmark identification. Thus, workflow context is "built" into the movie presets and meta data. Provided workflow context in the form of metadata and movie presets may be used to determine additional constraints For example, in this workflow context approach, the intended focal points and features of the movie may be used to efficiently determine the landmarks. For example, an intended focal point of a movie may be to provide a view of the spine from top to bottom. Scan data representative of the patient's body including the entire spine may be the initial data set. Landmark identification in this example may then be a set of positional points associated with each vertebra. A general expected anatomical order of the spinal column is known such that sets of classifiers associated with spinal regions (e.g., cervical, thoracic, lumbar, etc.) are applied to regions of the scan. Detection of one or more landmarks in a region may constrain the region of the adjacent spinal region and so on. A base layer of spinal region may then be used to determine sets of classifiers within each spinal region, such that the next hierarchical set of classifiers is applied to the identified region. In this example, sets of classifiers may be established for each vertebra and applied based on the expected vertebra order, and/or associated region. Expected landmarks that are not detected in the scan data may additionally be provided as input. For example, in landmark identification of the spine from top to bottom, portions of missing vertebrae or entire vertebrae may be missing, damaged, or unidentifiable based on limitations of the scan data or the condition of the patient. Movie parameters may be used to identify whether the absence of information is an intended focal point or may be identified as an obstruction that should be removed.

Identified landmarks provide a selection of points from which key values may be selected. Key values are selected landmark points or positional points based on identified landmark points. Key values represent positional points describing relevant landmarks for the movie module 124. Positional points are representative of an outline or path from which the movie may be constructed. Positional points represent the order and path that will be presented in the movie. Movie images are generated by establishing parameters for the relevant scan data from which to generate movie image frames. The movie module 124 then detects relevant identified landmarks based on positional points in the specified order.

Landmarks associated with the scan data thus define a local frame of reference such that movie parameters may be determined based on the scan data. For example, the local frame of reference is used to construct and establish the "camera" perspective (e.g., define the camera focal point and frustum). A frame of reference can be defined from landmark points, landmark planes, or three or more anatomical landmark points representing a plane. A landmark point, an orientation relative to the patient, and/or a physical space size around the point is used to compute a camera frustum. Patient coordinate system (e.g., anterior, posterior, left, right, head, foot) is used to determine orientation. Alternatively, other coordinate systems may be used. A landmark plane (e.g., as detected plane through a structure), and a physical space size around the landmark point is then used to determine the camera frustum. Once a plane is detected from the anatomy, the plane defines a point and a vector in a local coordinate frame within the patient coordinate system which can fully describe the camera. Landmark planes may be determined using three or more anatomical landmark points representing a plane.

Computation of Camera Parameters

Key values may be associated with anatomical landmarks. The desired movie output may be interested in retaining a centered view of a particular region of the patient scan. The camera perspective may be optimized such that the field of view remains centered on a portion of the anatomy that moves throughout the cycle. Alternatively, the field of view may be set such that movement of the anatomy during the cycle does not affect the field-of-view. Accordingly, movement of the desired anatomy during the cycle can be observed while the camera perspective remains constant.

Identified landmarks transformed to the patient coordinate system establish the frame of reference for the generation of individual movie image frames. Sequences of movie frame images are unified using location of the identified landmark within the frame of reference such that individual frames are interpolated accordingly. Image processing of the data scan may remove unnecessary artifacts or anatomical features. For example, portions of the anatomy appearing in the scan data obscuring the anatomy of interest may be segmented from the scan data so that movie images may be rendered featuring only portions of interest. To generate the movie, the image data and any derived data to be visualized are added to the scene. The scene is configured to render at the specified movie quality such as image resolution. Specified movie frame rate is determined based on time steps specified in the movie descriptor by converting the movie descriptor into frame indices. The associated key value for each descriptor parameter is assigned to corresponding movie image frames. The rendering parameters and any visibility parameterization are applied to the scene and are ready for the rendering engine to convert the scene to images. For each frame, each parameter in the descriptor is interpolated between the key values, updated values are applied to the scene and renders. The resulting sequence of image frames are sent to a movie encoder to produce a movie file with the desired compression level.

Some landmarks specified for specific key value frames may potentially fail to be detected in the scan data. The processor may indicate a rendering failure or the absent key value may be approximated by interpolation of adjacent key values.

Rendering and Movie Generation

The output movie file may be complete as a movie for illustrative purposes. The output movie file may also be provided in a format such that a custom movie player or medical imaging program allows for further selection of points of interest. Processor 120 may include specialized programs for viewing, marking, or further interacting with the rendered movie. Medical professionals may use custom movie players allowing for selection of points of interest. The points of interest are provided by the user selecting specific 2D coordinate points on the image of specific frames. The coordinate points, the frame index, movie frame rate descriptors, data sets, and corresponding movie descriptors are provided back to the movie generation software module, where the specific frame parameter for the given frame index is recomputed and the scene that was used to generate that frame may be reconfigured. The specific selected 2D coordinate points are re-rendered to retrieve the selected point in the patient coordinate space. The patient coordinate points can then be correlated with specific pixels within the original medical image data. This selected pixel information can then be further used by another medical image viewer to provide further interactive exploration of the data if desired.

The generated movie may also include color markings, identification markers, text, scale, direction or other information associated with the movie displayed on the movie using an overlay. The overlay is a graphic, pixel coloring, and/or other indicator of the regions, anatomy, or other identified portions or objects rendered by movie module 124 of processor 120. Overlay markings may be generated, by movie module 124, landmark module 122, another module of processor 120, and/or rendered based on information included in data from medical imaging device 110, landmark information associated with data from landmark module 122, or imported from other components in the system including other processors or databases.

Figure 3A:
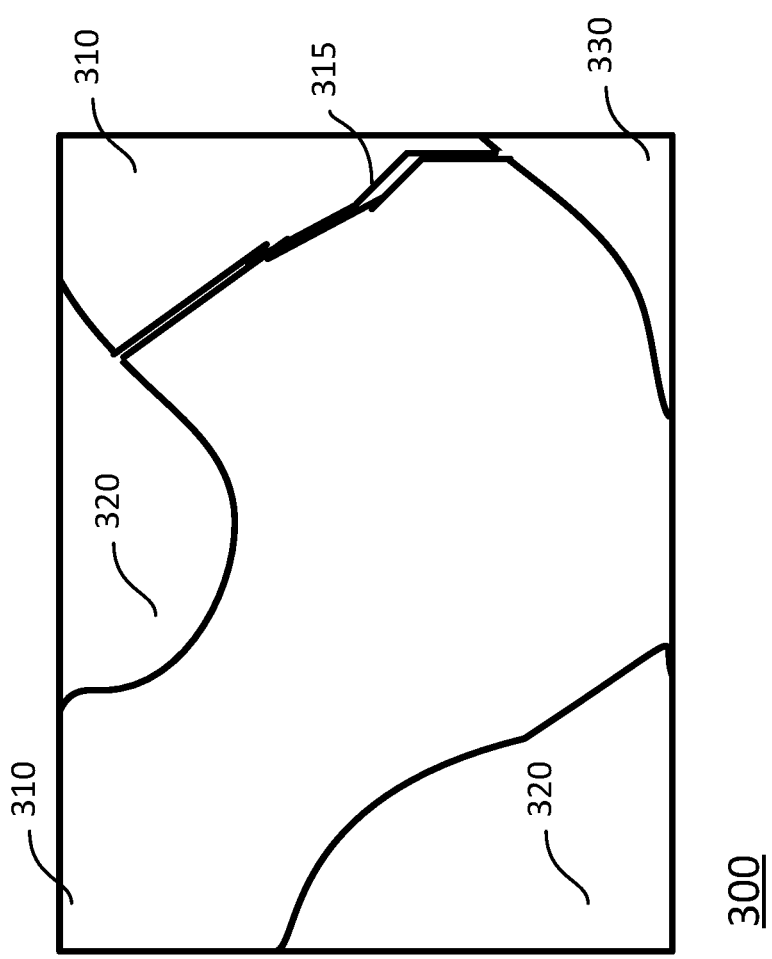
FIGS. 3A-3D are illustrations representative of portions of the method of FIG. 2.

FIG. 3A is an illustration of depicting scan data in accordance with one embodiment for generating anatomically specific movie driven medical image review. The frame of data 300 represents scan data received from a medical imaging device 110. Item 310 may be representative of a patient's bone with fracture 315. Portions 320 and 330 are representative of other objects detected in the scan. The desired medical image review may be to assess fracture 315 in further detail.

Figure 3B:
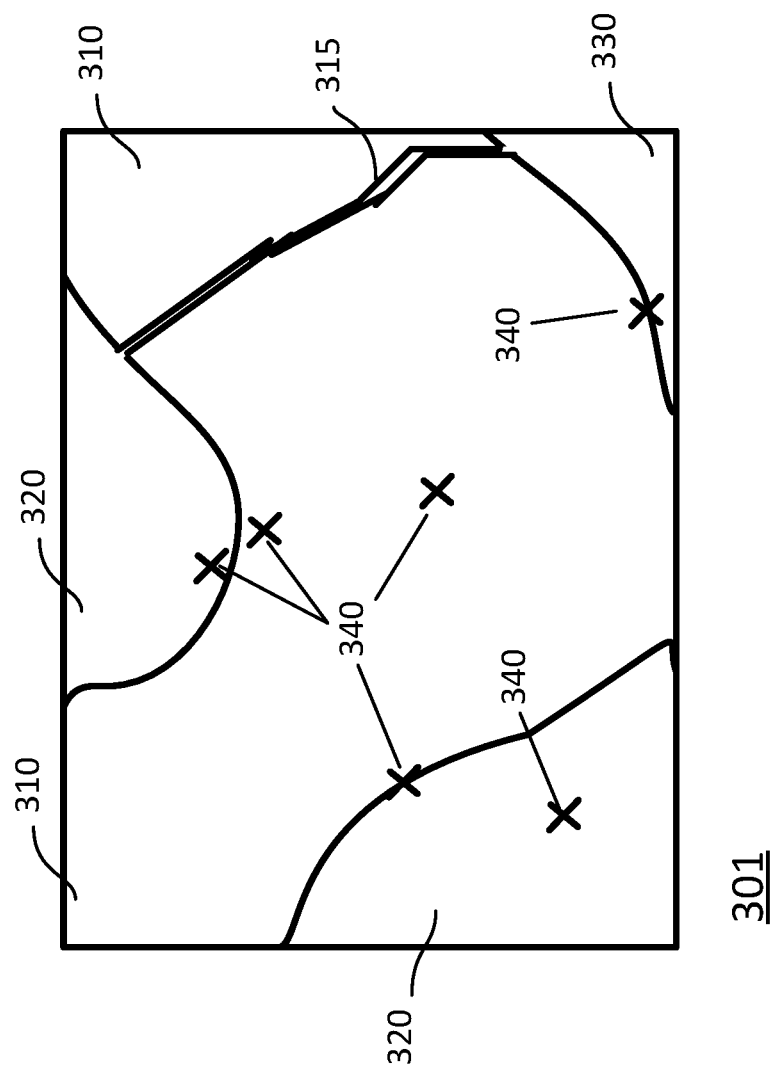

FIG. 3B is an illustration of the scan data of FIG. 3A with landscape identification points 340 identified. Frame of data 301 represents the scan data of FIG. 3A following landscape identification resulting in the identified landscape points represented by items 340. Landmark identification as depicted has identified several points along 310 as well as landscape identification of item 320.

Figure 3C:
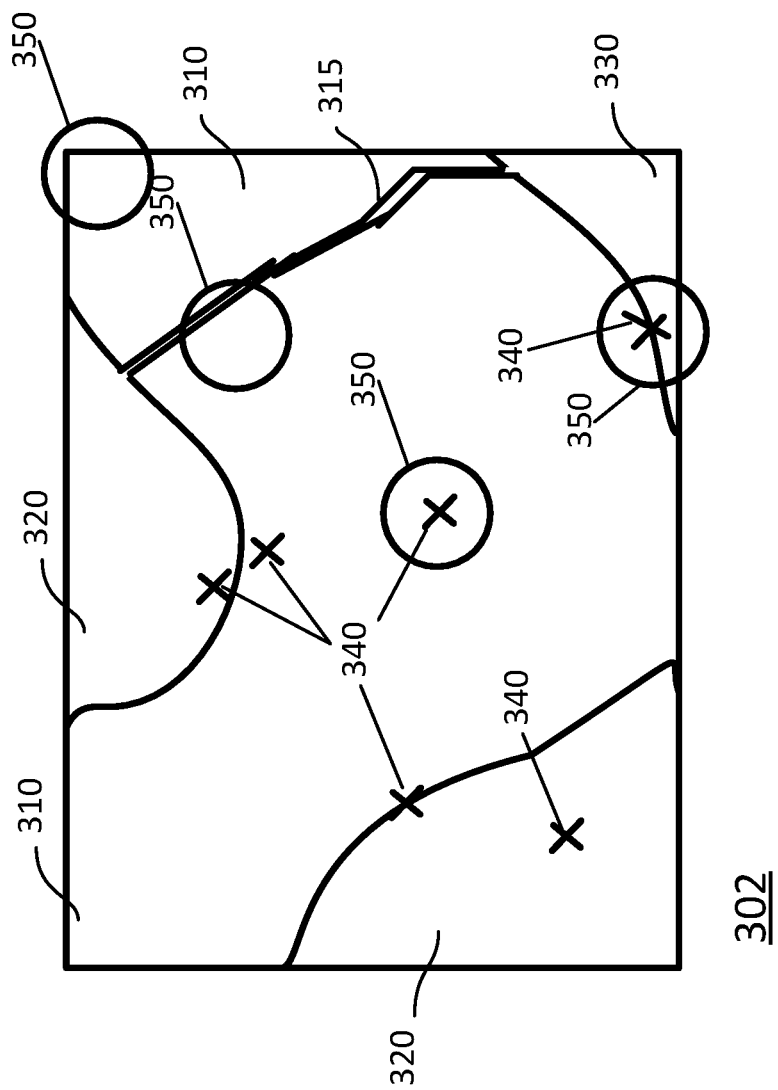

FIG. 3C is an illustration of the scan data after key values have been selected to guide the movie data. Key values and positions in frame 302 is represented by circles 350. Key value of circles 350 is located in the center of the depicted circle. Some key values may coincide with the location of landmark identification. Other key values such as the key value along fracture 315 may be determined relative to other landmark identification points. Within the movie module, key points may be used to determine the path of the camera perspective when generating movie frames. The intended path depicted in frame 302 may begin in the lower right corner of the frame and proceed through the key values ending at the upper right frame.

Figure 3D:
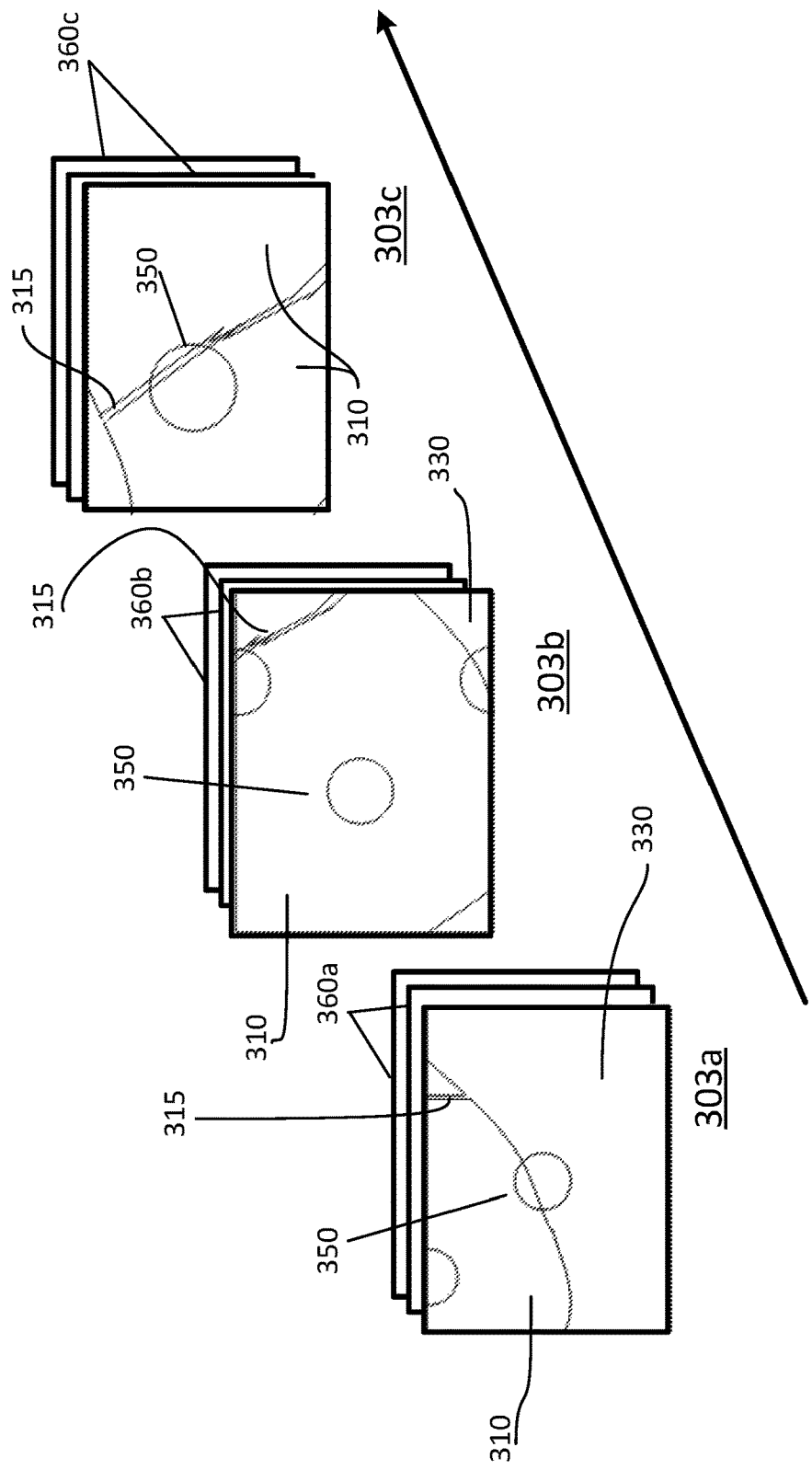

FIG. 3D is an illustration of the rendering of scan data based on positional points to create a movie. Frames 303A, 303B, 303C are representative of generated movie frames showing movie frames generated from perspectives based on key values 350. 303A illustrates camera centering around first key value. 303B is representative of the second key value 350. 303C is representative of the third key value. Generation of movie frames is intended for display and sequence in the direction of the arrow. Additional frames 360A, 360B, and 360C, may be generated to provide smooth transitions from one key value to the next key value and so on. Interpolation may be combined with scan data in order to generate additional frames 360A-C.

Descriptors for movie scene parameters may be assigned to specific time steps within the movie sequence as a key value. Each parameter is also defined with a method for interpolation between key values. For example, quaternion interpolation for camera orientations, linear/spline interpolation of key values, or no interpolation at all (Boolean values). Movie generation preset descriptors may additionally specify special effects such as motion blur, and/or frame transition effects between major key frames.

Movie Playback, Analysis, and Subsequent Movie Generation

Custom movie players may further allow the user alter the composed movie during playback. All parameters that were used to generate a particular frame are transferred back to the interactive medical viewer. The user can change these parameters interactively to change an existing key frame or insert a new custom key frame. The frames influenced by the changed inserted key frame will then be rendered and a new movie will be encoded by the system.

Generation and rendering of the movie made to be dependent on presets selected for a particular medical examination purpose. For example, lighting parameters contrast, brightness, and other features of the rendered movie frames may be determined to optimize a medical exam for fracture, movement, or other desired feature for medical review. Text labels of the identified anatomy derived from the detected anatomical landmarks, for example, could be a useful preset option.

The movie player may also provide mechanisms to add annotations to individual frames or a sequence of frames. Such annotations can be specified in more detail in the movie frames using user-defined geometric objects such as rectangles ellipsoid's or other geometric shapes to highlight regions of interest. The user may also manipulate the speed of portions of the movie. Additional intermediate frames may then be rendered between the key frames and re-encoded.

Optimization of the field of view and optimization of playback of the movie landmarks to find by the landmark module preferably capture key transitions such that the interpolation between adjacent key values would not produce undesirable jobs and visual parameters or produce camera paths that may go through other objects. The latter can be avoided by providing additional points along the path that go around the obstructing object. The points and the obstructing object could be estimated from known landmarks based on standard anatomical models. Another approach for obstruction avoidance is to incorporate collision detection of the camera along each frame to detect if the camera field of view collides with any defined undesirable objects and subsequently deflect from the colliding object to insert new key values during the movie production.

Optimization may include temporal filtering and may trigger the interpolation of intermediate frames to provide smooth transitions by changing the frame rate. Temporal filtering may also include removal of intermediate frames to increase the frame rate.

Optimization of the movie may include compensating for gaps in data scan information interpolation between frames lacking data. Information may be interpolated within a single image frame, or entire intermediate frames may be interpolated for smoothing of the video transition. Additional optimization may be achieved by applying smoothing algorithms to adjust and unify the frame of reference in the sequence of frames.

Optimization of camera movement may include creating smooth pans, reducing jumps, reducing camera jiggle to calculate a smooth pass. The camera path itself may be optimized to avoid obstructions or to highlight the region of interest. Key data point associated with identified landmark may provide a rough outline for a camera pan the sequence of the camera and relative location. The construction of the movie may be based on a series of points generation of the path, and optimization of generated movie image frames based on the scan data. Multiple paths may be determined to provide multiple movies. Based on camera presets and identified landmarks a best pass may be automatically selected with the field-of-view camera speed resolution and zoom may be optimized. Multiple renderings may be constructed and provided to the operator for selection. Selections may be provided to the user. Based on selected best views or clips, additional smoothing interpolation and other techniques may be applied to create smooth transitions between selected video clips or selected best path.

Application of System Workflow to Time Based Scan Data

Method 200 may be applied to time based scan data by first generating a general 3D model from scan data representing a single time stamp. The general 3D model serves as a base to generate the 3D model for each of the remaining time stamps. Computational efficiency is achieved for imaging data that does not change significantly from one-time stamp to the next. Instead of performing the same landmark identification on the scan data set at each time stamp to determine position, the base 3D model can be applied to each timestamp. Any changes in landmark position may then be identified with minimal landmark identification computations because the general location of each landmark has an expected position. Only location changes in the landmarks need to be identified in the remaining scan sets at the remaining time stamps. Small changes between timestamps may include small movements of the patient during the duration of the scan such as breath cycles, heartbeat or shifts in patient orientation during the scan. Undesired movement components may be removed from the rendering equation to smooth transitions between multiple data sets at different timestamps. Landmarks for temporally based scan data may include parameters associated with the target region that may be applied. Target regions that are applied to the entire sequence of data sets may be indicated by one preset associated each data scan time stamp. By identifying a landmark target, consistent field-of-view may be maintained over time regardless of shifts of the patient during examination. Accordingly, the relative location of the landmark may need to be updated in subsequent timestamps to accommodate such movement. The data set or image used to determine the set of filters and parameters for temporally based scan may be the first image in time or may be selected by the user based on the perceived preferred set of scan data with more information, or a most suitable for representative data set may be selected by the user.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for generating anatomically specific movie driven medical image review, the method comprising:
   receiving scan data representing an anatomy of a patient;
   receiving a movie generation preset selection associated with the scan data;
   detecting a plurality of anatomical landmarks associated with positional points within the scan data; and
   generating a movie of the patient along a movie path, the movie comprising a continuous sequence of movie image frames based on the scan data along the movie path, wherein the movie path is determined based on an order of the positional points associated with the anatomical landmarks, the generating being based on the scan data, the movie generation preset, and the anatomical landmarks, wherein a viewing perspective of the movie is automatically controlled based on the anatomical landmarks detected within the scan data as the movie of the patient is generated, wherein automatically controlling the viewing perspective of the movie includes changing a direction of the viewing perspective of the movie as passing from a view of one of the anatomical landmarks along the movie path to another view of another of the anatomical landmarks along the movie path.

2. The method of claim 1, wherein detecting anatomical landmarks within the scan data further comprises:
   applying at least one first classifier to the scan data; and
   identifying at least one first landmark based on the at least one first classifier.

3. The method of claim 2, further comprising:
   selecting a portion of the scan data based on the identified landmark;
   applying at least one second classifier to the determined portion of the scan; and
   identifying at least one second landmark based on the at least one second classifier.

4. The method of claim 2, further comprising:
   selecting the at least one first classifier based on the movie generation preset.

5. The method of claim 1, wherein generating the movie of the patient based on the scan data, the movie generation preset, and the anatomical landmarks further comprises:
   determining parameters of the movie based on the movie generation preset.

6. The method of claim 1, wherein generating the movie of the patient based on the scan data, movie generation preset, and the anatomical landmarks further comprises:
   optimizing the movie path based on the identified landmarks.

7. The method of claim 1, wherein scan data includes data sufficient to create a three-dimensional model.

8. The method of claim 7, wherein scan data further includes a temporal parameter.

9. The method of claim 1, wherein automatically controlling the viewing perspective of the movie based on the anatomical landmarks comprises:

defining a local frame of reference for each of the anatomical landmarks; and defining a viewing perspective of the movie from the local frames of reference.

10. The method of claim 9, wherein defining a local frame of reference for each of the anatomical landmarks comprises:

identifying three or more anatomical landmark points for each of the anatomical landmarks;

determining a landmark plane for each of the anatomical landmarks based on the identified landmark points;

determining an orientation relative to the patient of each landmark plane for each of the anatomical landmarks; and defining a local frame of reference for each of the anatomical landmarks based on the orientation relative to the patient of each landmark plane for each of the anatomical landmarks.

11. In a non-transitory computer readable storage medium having stored therein data representing instructions executable by a programmed processor for generating anatomically specific movie driven medical image review, the storage medium comprising instructions for:

receiving scan data representing an anatomy of a patient;

receiving a movie generation preset associated with the scan data;

applying at least one classifier to the scan data based on at least one parameter of the movie generation preset associated with the scan data;

identifying at least one first landmark and at least one second landmark within the scan data based on the at least one classifier, wherein the at least one first landmark and the at least one second landmark are associated with positional points; and generating a movie along a movie path, the movie comprising a continuous sequence of movie image frames based on the scan data along the movie path, wherein the movie path is determined based on an order of the positional points associated with the at least one first landmark and the at least one second landmark, the generating being based on the scan data, the movie generation preset, and the at least one identified first landmark, wherein a viewing perspective of the movie is automatically controlled based on the at least one identified first landmark as the movie is generated, wherein automatically controlling the viewing perspective of the movie includes changing a direction of the viewing perspective of the movie as passing from a view of the at least one first landmark along the movie path to another view of the at least one second landmark along the movie path.

12. The non-transitory computer readable storage medium of claim 11, wherein identifying at least one first landmark within the scan data further comprises:

selecting at least one second classifier based on the at least one identified first landmark.

13. The non-transitory computer readable storage medium of claim 12, further comprising:

selecting a portion of the scan data based on the at least one identified first landmark;

applying the at least one second classifier to the selected portion of the scan; and identifying the at least one second landmark based on the at least one second classifier within the selected portion of the scan.

14. The non-transitory computer readable storage medium of claim 12, further comprising:

selecting the at least one second classifier based on the movie generation preset.

15. The non-transitory computer readable storage medium of claim 11, wherein generating a movie based on the scan data, the movie generation preset, and the at least one identified first landmark further comprises:

determining parameters of the movie based on movie generation presets.

16. The non-transitory computer readable storage medium of claim 11, wherein generating a movie based on the scan data, the movie generation preset, and the at least one identified first landmark further comprises:

optimizing the movie path based on the at least one identified first landmark.

17. The non-transitory computer readable storage medium of claim 11, wherein scan data includes data sufficient to create a three-dimensional model.

18. The non-transitory computer readable storage medium of claim 17, wherein scan data further includes a temporal parameter.

19. A system for generating anatomically specific movie driven medical image review, the system comprising:

an imaging system configured to collect scan data representing an anatomy of a patient;

a processor configured to:

detect anatomical landmarks associated with positional points represented by the scan data; and generate a movie along a movie path rendered from the scan data, the movie comprising a movie sequence field of view of continuous movie image frames based on the scan data along the movie path, wherein the movie path is determined based on an order of the positional points associated with the anatomical landmarks, the rendering being based on the anatomical landmarks and a preset group of parameters for the scan data, wherein a viewing perspective of the rendered movie is automatically controlled based on the anatomical landmarks as the movie is generated, wherein automatically controlling the viewing perspective of the rendered movie includes changing a direction of the viewing perspective of the movie sequence field of view as passing from a view of one of the anatomical landmarks along the movie path to another view of another of the anatomical landmarks along the movie path.

20. The system of claim 19, the processor further configured to:

generate a multidimensional model based on the detected anatomical landmarks and scan data.

21. The system of claim 20, the processor further configured to:

determine the movie path as a path of the movie sequence field of view of the multidimensional model based on the preset group of parameters and the anatomical landmarks.

22. The system of claim 21, wherein the processor is further configured to:

determine obstructions within the path of the movie sequence field of view;

construct the path of the movie sequence to exclude the determined obstructions within the movie sequence field of view; and interpolate alternative imagery based on scan data and images of the movie sequence.

* * * * *